United States Patent [19]

Matsuo et al.

[11] Patent Number: 4,704,359
[45] Date of Patent: Nov. 3, 1987

[54] PROTEASE AND PROCESS FOR PRODUCTION AND USE THEREOF

[75] Inventors: Hisayuki Matsuo; Kensaku Mizuno, both of Miyazaki; Takaharu Tanaka, Osaka, all of Japan

[73] Assignee: Suntory Limited, Osaka, Japan

[21] Appl. No.: 917,210

[22] Filed: Oct. 9, 1986

Related U.S. Application Data

[62] Division of Ser. No. 722,356, Apr. 12, 1985, Pat. No. 4,650,763.

[30] Foreign Application Priority Data

Apr. 14, 1984 [JP] Japan .................................. 59-73875

[51] Int. Cl.[4] ........................ C12P 21/06; C12R 1/865
[52] U.S. Cl. ......................................... 435/69; 435/949
[58] Field of Search ................................... 435/69, 949

[56] References Cited
PUBLICATIONS

Kurjan J. et al., *Cell*, 30, 933–943, (1982).
Julius D. et al., *Cell*, 32, 839–852, (1983).
Fletcher et al., *J. Cell Biol.*, 90, 312–322, (1981).
Loh Y. P. et al., *Proc. Natl. Acad. Sci. U.S.A.*, 79, 108–112, (1982).
Mizuno et al., *Biochem. Biophys. Res. Commun.*, 108, 1235–1242.
Lindberg I. et al., *Biochem. Biophys. Res. Commun.*, 106, 186–193, (1982).
Evangelista R. et al., *Biochem. Biophys. Res. Commun.*, 106, 895–902, (1982).
Fricker L. D. et al., *Proc. Natl. Acad. Sci. U.S.A.*, 79, 3886–3890, (1982).

*Primary Examiner*—Lionel M. Shapiro
*Attorney, Agent, or Firm*—Burns, Doane, Swecker and Mathis

[57] ABSTRACT

Disclosed is a new protease having the following properties: (1) it is able to hydrolitically cleave a peptide bond between two adjacent basic amino acids in a peptide chain; (2) it has a molecular weight of about 43,000 as determined by electrophoresis; (3) it is inhibited by phenylmethylsulphonyl fluoride and diisopropyl fluorophosphate, but is not inhibited by monoiodoacetate, p-chloromercuribenzoic acid, ethylenediaminetetraacetic acid, 1,10-phenanthroline, tosyl-L-lysine chloromethyl ketone, and leupeptin. The protese can be produced by culturing *Saccharomyces cerevisiae*, and recovering purification by conventional methods, and is useful as a processing enzyme for conversion of a prohormone to an active hormone.

6 Claims, 3 Drawing Figures

PROTEASE AND PROCESS FOR PRODUCTION AND USE THEREOF

This application is a division of application Ser. No. 722,356, filed Apr. 12, 1985, now U.S. Pat. No. 4,650,763, issued Mar. 17, 1987.

BACKGROUND OF THE INVENTION

1. Field of the Invention

The present invention relates to a novel protease which hydrolytically cleaves a peptide bond between two adjacent basic amino acids present in a peptide chain, and a process for production of the protease.

2. Description of the Related Art

Usually two basic amino acids are adjacent in a prohormone, i.e., a precursor of peptide hormone, such as adrenocorticotrophic hormone, melanocyte-stimulating hormone, β-lipotropin, β-endorphin, α-neoendorphin, insulin, or the like. In such cases, the prohormone is activated to its active hormone by cleavage of a peptide chain of the prohormone at an N-side, C-side, or middle of the adjacent two basic amino acids, and the activation is carried out by a corresponding enzyme protease.

Recent progress in the field of genetic engineering has brought to light the possibility of microbial production of many kinds of higher animal hormones, wherein mRNA's coding for a prohormone are obtained from an animal, cDNAs are prepared from the mRNA, the cDNAs are screened, and the selected cDNA is incorporated into a appropriate vector which is then transformed into a host. In such a case, often an inactive prohormone rather than active hormone is expressed. Therefore, to obtain an active hormone, the prohormone must be artificially processed by a processing enzyme. In such a situation, the above-mentioned proteases are of practical interest.

Kurjan J. et. al., *Cell*, 30, 933–943, (1982); and Julius D., et al., *Cell*, 32, 839–852 (1983) describe a membrane-bound dipeptidyl aminopeptidases which processes a precursor polypeptide to form a yeast α-factor. This enzyme cleaves a carboxyl side of repeating-X-Ala-sequences, however, this action is different from that of the protease of the present invention.

Proteases from an animal that cleave a peptide bond between two adjacent basic amino acids in a peptide chain are described by Fletcher et. al., *J. Cell Biol.*, 90, 312–322 (1981); Loh Y. P. et. al., *Proc. Natl. Acad. Sci. U.S.A.*, 79, 108–112 (1982); Mizuno et. al., *Biochem. Biophys. Res. Commun.*, 108, 1235–1242 (1982); Lindberg I. et. al., *Biochem. Biophys. Res. Commun.*, 106, 186–193 (1982); Evangelista R. et. al., *Biochem. Biophys. Res. Commun.*, 106, 895–902 (1982); and Fricker L.D. et. al., *Proc. Natl. Acad. Sci. U.S.A.*, 79, 3886–3890 (1982). All of these enzymes are different from the protease of the present invention in detailed properties, including specificity to substrates and response to various inhibitors. Moreover, these known enzymes are difficult to produce industrially because they are derived from animals.

SUMMARY OF THE INVENTION

The present invention provides a novel protease which hydrolytically cleaves a peptide bond between two adjacent basic amino acids present in a peptide chain.

The present invention also provides a process for production of the protease, and a description of the use of the portease.

DESCRIPTION OF THE PREFERRED EMBODIMENT

During their search for a novel protease which converts a prohormone to an active hormone, and which can be industrially produced, the present inventors screened various microorganisms and found strains of yeast Saccharomyces which produce the desired protease.

Properties of the protease

The protease has the following properties:

(1) Action: hydrolytically cleaves a peptide bond between two adjacent basic amino acids present in a peptide chain.

(2) Specificity to substrates: for example, it cleaves arrowed sites of the following peptides:

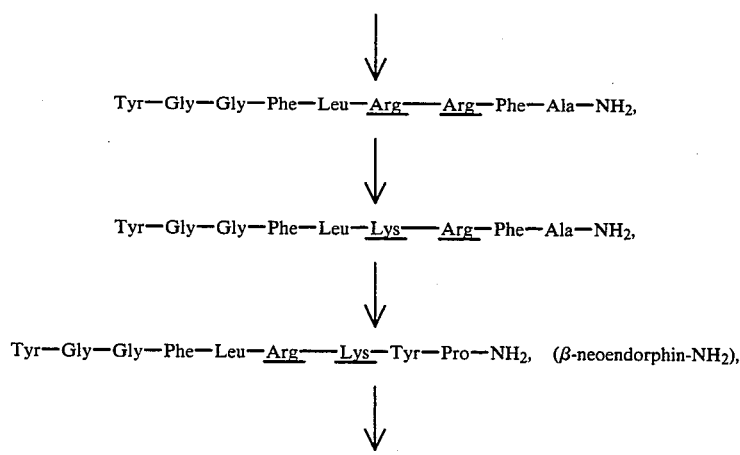

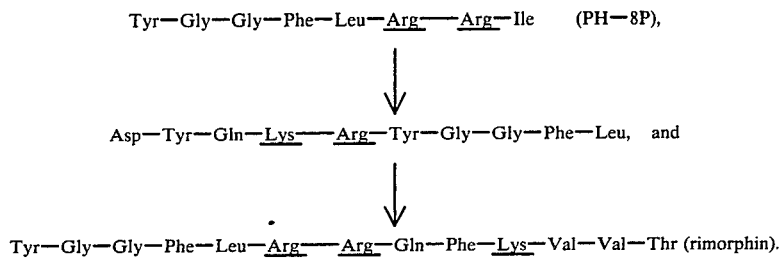

Tyr—Gly—Gly—Phe—Leu—Arg——Arg—Gln—Phe—Lys—Val—Val—Thr (rimorphin).

However, it does not cleave the following peptides:
Tyr-Gly-Gly-Phe-Leu-Arg, Iyr-Gly-Gly-Phe-Leu-Lys, Tyr-Gly-Gly-Phe-Leu-Arg-NH$_2$, Tyr-Gly-Gly-Phe-Met-Arg-Phe, Tyr-Gly-Gly-Phe-Met-ArgPhe-NH$_2$, Tyr-Gly-Gly-Phe-met-Arg-Gly-Leu, Tos-Arg-OMe(-TAME), and Bz-Arg-MCA.

As seen from the above, the present protease does not hydrolyze a peptide bond positioned either side of a basic amino acid having no adjacent basic amino acid. Also, when a peptide chain has a basic amino acid at its carboxyl terminal, and a carboxyl group of the basic amino acid is amidated, the amide bond is not cleaved by the present protease. Therefore, the present protease is an endopeptidose.

(3) Molecular weight: about 43,000 as measured by electrophoresis.

Figure 1:
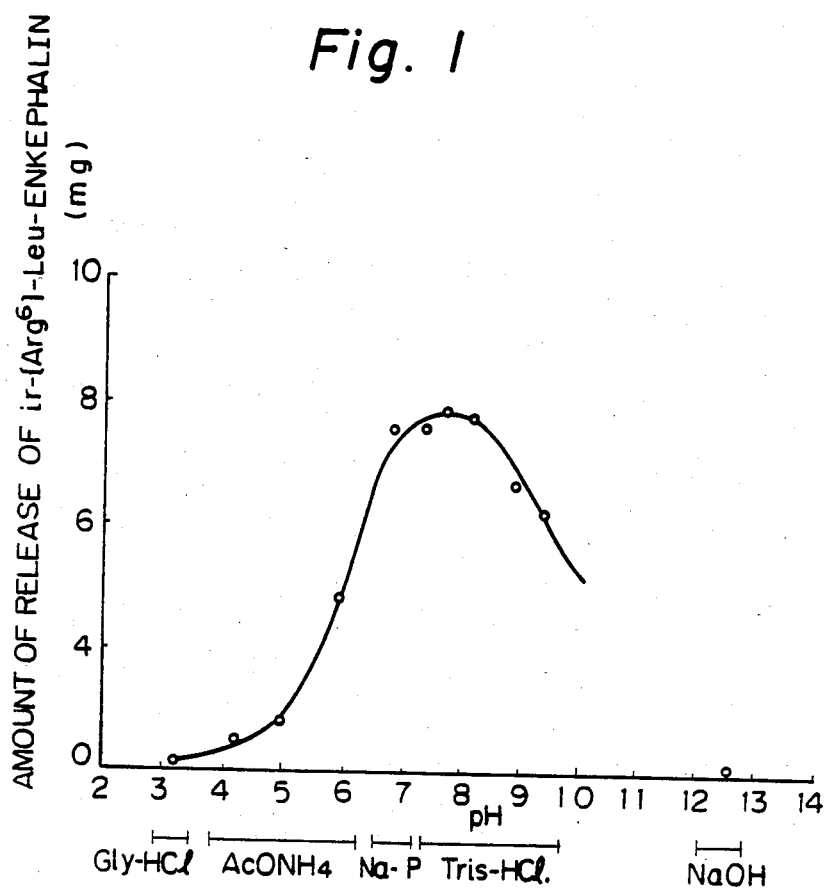
FIG. 1 is a graph showing a pH-activity curve of the protease of the present invention.

(4) Optimum pH and stable pH range: the protease has an optimum pH of about 7.5, and is stable within a range of pH 5 to pH 10, as shown in FIG. 1.

(5) Optimum temperature and range of temperature for activity: optimum temperature is about 37° C.; and range of temperature for activity is between 20° C. and 45° C.

(6) Response to inhibitors: the protease is completely inhibited by serine-protease inhibitors such as phenylmethylsulphonyl fluoride and diisopropyl fluorophosphate at a concentration of $2 \times 10^{-4}$ M. Thiol-protease inhibitors such as monoiodoacetate and p-chloromercuribenzoic acid and metal chelators such as ethylenediaminetetraacetic acid and 1,10-phenanthroline at $10^{-3}$ M have no effect on the enzyme activity, and the protease is resistant to the general trypsin inhibitors such as tosyl-L-lysine chloromethyl ketone ($10^{-3}$ M) and leupeptin ($10^{-4}$ M).

These results indicate that, although the present protease falls into the category of a serine-type protease, it is distinct from pancreatic trypsin and other related proteases, and thus is a novel protease.

Process for production of the protease

The protease of the present invention may be produced by culturing a yeast belonging to genus Saccharomyces capable of producing the required protease, harvesting the cultured cells, and obtaining the protease from the harvested cultured cells.

As the yeast, any strain of Saccharomyces capable of producing the protease can be used. Examples of such strain are those belonging to *Saccharomyces cerevisiae*, such as *Saccharomyces cerevisiae* X-2180-1B (ATCC-26787) which is a representative of α-mating type strains, and *Saccharomyces cerevisiae* X-2180-1A (ATCC-26786) which is a representative of a-mating type strains. These strains are available in the public domain, without limitation, from ATCC.

For production of the protease, one of the above-mentioned yeasts is cultured in a medium in which the yeast can grow and produce the protease. The medium contains one or more nitrogen sources such as peptone, casamino acid, meat extract, yeast extract, corn steep liqueur, soy bean powder, amino acids, or ammonium salts and the like; one or more carbon sources such as glucose, dextrin, or cane molasses; one or more optional minerals such as phosphate salts, magnesium sulfate, or manganese sulfate; and one or more optional growth factors such as vitamins, or nucleic acid-related compounds. The medium may be a solid medium, but to obtain a large amount of cells, a liquid medium is preferably used.

Culturing is preferably carried out under an aerobical condition accomplished by shaking the liquid medium, or by agitating the medium and carrying out aeration in a fermentor. When culturing is carried out in a liquid medium with agitation and aeration, the addition of an antifoam such as silicone-antifoam, polypropylene derivatives, or soy bean oil is often effective in enhancing the production of the protease. For the culturing, a one-step culturing wherein a production medium is immediately inoculated with a small amount of inoculam yeast cells can be carried out, however, a multi-step culturing is preferable wherein a small amount of inoculam is inoculated into a preculture medium, and the preculture is inoculated into a large amount of production medium.

The temperature, term, and pH value for culturing are determined in such a manner that maximum production of the protease is attained. For example, the culturing is preferably carried out at 25° C. to 30° C. for 2 to 3 days, maintaining the pH at about 5.

As the protease of the present invention is accumulated in cultured cells, in a process for obtaining the protease, the cultured cells are first separated from cultured medium, disrupted to release the protease, and the released protease then recovered. The separation of cells can be carried out according to a conventional method, such as centrifuge or filtration of the cultured medium containing the cells. The separated cells are washed with water, or an isotonic aqueous solution such as saline or a buffer solution such as a phosphate buffer solution, and resuspended in the same solution. The washed cells are then disrupted by a conventional means, such as a physical or mechanical means, e.g., a sonicator or milling machine such as Dynomill cell disrupture (W.A.B. Engineering Works (Basle Swiss)), or an enzymatical means such as lysed by incubation with Zymolyase-60000 (Seikagaku Kogyo Ltd., Tokyo Japan), to release the protease. The mixture thus obtained contains the released protease and cell debris, and is centrifuged or filtrated to remove the cell debris and other particles, if present. The supernatant or filtrate thus obtained containing the protease is added with a solid precipitating agent such as ammonium sulfate to precipitate the protease. Preferably ammonium sulfate is added until a 90% saturation of ammonium sulfate is reached. Alternatively a liquid precipitating agent such as acetone or ethanol may be added to the supernatant or filtrate to precipitate the pretease. The treated supernatant or filtrate is then centrifuged or filtered to recover a crude protease preparation.

For further purification, the crude preparation is redissolved in water, or preferably in a buffer solution such as a phosphate buffer or Tris-HCl buffer with a pH of about 7.5 to 8.0, and the solution is dialyzed against a buffer solution, e.g., the above-mentioned buffer solution, to eliminate the precipitating agent added previously and other low molecular materials. The dialysate thus obtained, if necessary after concentration, is subjected to a column chromatography. Preferably, the dialysate is applied to a column containing DEAE Sephadex A-25, and eluted with 0.25 M sodium chloride to obtain fractions containing the protease. The active fractions are combined and applied to a column of, e.g., Sephacryl S-300 (Pharmacia Fine Chemicals Sweden), for gelfiltration to obtain fractions containing purified protease. The purified fractions are combined, desalted, concentrated, and lyophilyzed to obtain a purified protease preparation.

Measurement of activity of the protease

The activity of the present protease is measured using a synthesized enkephalin peptide (Tyr-Gly-Gly-Phe-Leu-Arg-Arg-Phe-Ala-NH$_2$) as a substrate. To 0.1 ml of a substrate solution containing 1 mM EDTA, 1 nM DTT, and 0.1 mM substrate, 0.02 ml of a sample is added, the mixture is incubated for 2 hours at 37° C., and heated for 10 minutes at 100° C. to terminate reaction. The amount of a product (Tyr-Gly-Gly-Phe-Leu-Arg) formed during the incubation is measured by radioimmunoassay using antisera against the product. One unit is defined as an amount of the protease which forms 1 $\mu$M ($\mu$ mole) of Tyr-Gly-Gly-Phe-Leu-Arg from the enkephalin peptide (Tyr-Gly-Gly-Phe-Leu-Arg-Arg-Phe-Ala-NH$_2$) for one minute.

Use of the protease

As the protease of the present invention cleaves a peptide bond between two adjacent basic amino acids in a peptide chain, it can be used for various purposes wherein such cleavage is necessary. For example, as a cleavage site of most prohormones from higher animals includes two adjacent basic amino acids, when a prohormone produced by a transformant prepared by genetic engineering techniques is to be processed to an active hormone, the present protease can be used as a processing enzyme. Moreover, the present protease may be useful as a cleavage enzyme for sequencing a peptide chain.

EXAMPLE

The present invention will now be further illustrated by, but is by no means limited to, the following example.

100 ml of a liquid nutrient medium containing 3 g/l yeast extract, 3 g/l malt extract, 5 g/l Polypepton (trade name; peptone, commercially available from Takeda Chemical Industries, Japan), and 10 g/l glucose was incorporated in a 500 ml Erlenmeyer flask, and the flask was autoclaved at 120° C. for 15 minutes. To the medium a piece of cell mass of Saccharomyces cerevisiae X2180-1B (ATCC 26787) cultured on an agar slant medium is inoculated, and incubated in a reciprocating shaker at 25° C. for 2 days to obtain an inoculam.

25 liters of a production medium with the same composition as above is incorporated into a jar-fermentor having a 50 liter volume, sterilized at 125° C. for 5 minutes, cooled, and inoculated with 500 ml (5×100 ml) of the above-mentioned inoculum. Culturing was carried out at 25° C. for 2 days with agitation at 200 rpm and aeration at 12 1/min. On the second day, 10 g/l of glucose was added, and the culturing was continued for an additional 2 days. After the culturing, the cultured medium was centrifuged to obtain 500 grams of wet cells.

The cells were washed two times with four liters of saline solution, and resuspended in the same solution.

Figure 2:
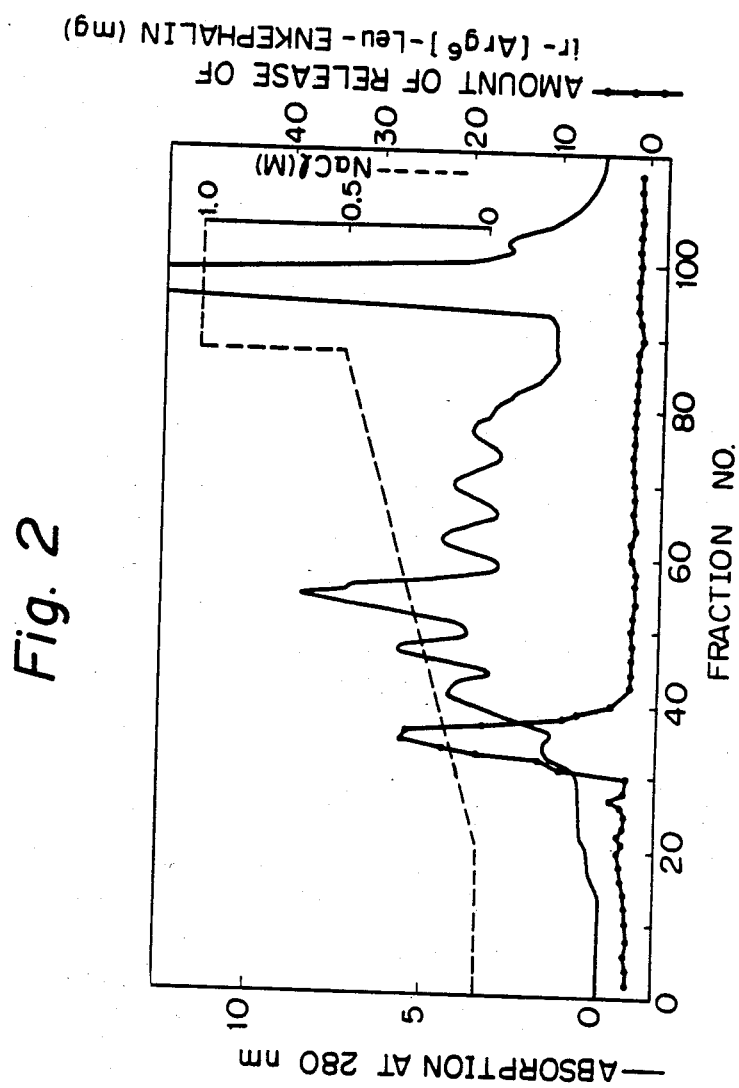
FIG. 2 is an elution profile in column chromatography with DEAE Sephadex G-50 during a purification process of the present protease.
Figure 3:
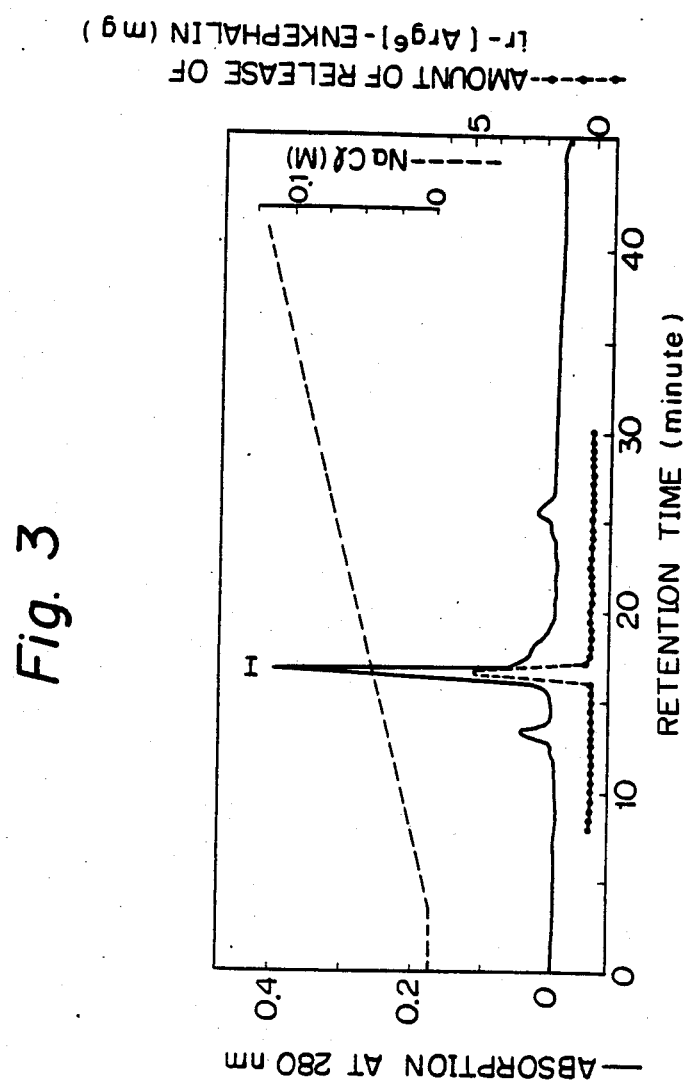
FIG. 3 is an elution profile in cation exchange high performance liquid chromatography (HPLC) with a Mono Q (Pharmacia Fine Chemicals AB, Sweden) column during the purification process of the present protease.

The cells were disrupted with a Dynomill cell disrupter to release the protease. The treated suspension was centrifuged to obtain a supernatant. To the supernatant, ammonium sulfate was added to the concentration until a 90% saturation of ammonium sulfate was reached to precipitate protein. The precipitate containing the protease was collected by filtration, dissolved into a 0.001 M Tris-HCl (pH 8.0) buffer, and the solution was dialyzed against the same buffer. The dialyzate containing the protease was applied to a column (6×50 cm) filled with DEAE Sephadex A-50 to adsorb the protease onto the column. The adsorbed materials were eluted using a concentration gradient elution with 0.0 to 0.5 M sodium chloride to obtain fractions. Active fractions were selected by radioimmunoassay, and the selected fractions were combined. The elution profile is shown in FIG. 2. The active fraction was applied to a column filled with Sephacryl S-300 equilibrated with 50 mM ammoniumacetate buffer pH 5.5 for further purification. The column was eluted with the above buffer and the elute was fractionated, and active fractions were selected by radioimmunoassay. The active fractions showed a single band in SDS-gel electrophoresis. To remove any trace of impurities, the combined active fraction was subjected to HPLC with a cation exchange column Mono Q HR 5-5 (registered trade mark of Pharmacia Fine Chemicals, 8 ml volume) eluting by a concentration gradient of 0.0 to 0.125 M sodium chloride at a flow rate of 1.0 ml/min. By the HPLC, purified protease fractions were obtained. The elution profile is shown in FIG. 3. The combined protease fraction was lyophilized to obtain 10 mg of pure protease. The protease showed a molecular weight of about 43,000 as measured by electrophoresis with SDS-polyacrylamide gel.

We claim:
1. A method of converting a prohormone to an active hormone comprising hydrolytically clearing said prohormone with a protease having the following properties:
(1) hydrolytically able to cleave a peptide bond between two adjacent basic amino acids in a peptide chain;
(2) having a molecular weight of about 43,000 as determined by electrophoresis; and
(3) inhibited by phenylmethylsulphonyl fluoride and diisopropyl fluorophosphate, but not inhibited by monoiodoacetate, p-chloromercuribenzoic acid, ethylenediaminetetraacetic acid, 1,10-phenanthroline, tosyl-L-lysine, chloromethyl ketone, and leupeptin.
2. The method according to claim 1, wherein the prohormone is an expression product from a transformant prepared by genetic engineering techniques.

3. The method according to claim 1, wherein the protease is produced by a process in which a yeast belonging to the genus *Saccharomyces* and capable of producing said protease is cultured in a nutrient meduim, the cultured cells are harvested from the cultured medium, the harvested cells are disrupted to release said protease, and said protease is recovered.

4. A method according to claim 3, wherein said yeast is *Saccharomyces cerevisiae*.

5. A method according to claim 4, wherein the *Saccharomyces cerevisiae* is *Saccharomyces cerevisiae* X2180-1B (ATCC 26787) or *Saccharomyces cerevisiae* X2180-1A (ATCC 26786).

6. A method according to claim 3 wherein the yeast is cultured in a liquid medium under aerobical conditions with agitation of the medium and aeration.

* * * * *